United States Patent [19]
Cleary

[11] Patent Number: 6,053,730
[45] Date of Patent: Apr. 25, 2000

[54] ORTHODONTIC FORCE MODULE WITH FRACTURE-RESISTANT COUPLING

[75] Inventor: James D. Cleary, Glendora, Calif.

[73] Assignee: 3M Innovative Properties Company, St. Paul, Minn.

[21] Appl. No.: 09/362,158

[22] Filed: Jul. 28, 1999

[51] Int. Cl.⁷ ................................................. A61C 3/00
[52] U.S. Cl. ............................................. 433/19; 433/18
[58] Field of Search ................................ 433/7, 18, 19, 433/24

[56] References Cited

U.S. PATENT DOCUMENTS

| | | |
|---|---|---|
| 473,040 | 4/1892 | Wilder . |
| 787,861 | 4/1905 | Shelp . |
| 934,958 | 9/1909 | Case . |
| 1,002,536 | 9/1911 | Montag . |
| 3,508,332 | 4/1970 | Armstrong . |
| 3,530,583 | 9/1970 | Klein et al. . |
| 3,618,214 | 11/1971 | Armstrong ................................ 433/19 |
| 3,690,003 | 9/1972 | Gerber . |
| 3,798,773 | 3/1974 | Northcutt . |
| 4,224,021 | 9/1980 | Foxman . |
| 4,382,783 | 5/1983 | Rosenberg . |
| 4,462,800 | 7/1984 | Jones . |
| 4,551,095 | 11/1985 | Mason . |
| 4,708,646 | 11/1987 | Jasper . |
| 4,795,342 | 1/1989 | Jones . |
| 5,074,784 | 12/1991 | Sterrett et al. . |
| 5,120,218 | 6/1992 | Hanson .................................... 433/19 |
| 5,183,388 | 2/1993 | Kumar . |
| 5,352,116 | 10/1994 | West ........................................ 433/19 |
| 5,358,405 | 10/1994 | Imai . |
| 5,435,721 | 7/1995 | Vogt . |
| 5,545,037 | 8/1996 | Takeshi ................................... 433/19 |
| 5,562,445 | 10/1996 | DeVincenzo et al. .................. 433/19 |
| 5,645,423 | 7/1997 | Collins, Jr. . |
| 5,645,424 | 7/1997 | Collins, Jr. . |
| 5,651,672 | 7/1997 | Cleary et al. . |
| 5,678,990 | 10/1997 | Rosenberg . |
| 5,711,667 | 1/1998 | Vogt . |
| 5,718,576 | 2/1998 | Schnaitter et al. . |
| 5,738,514 | 4/1998 | DeVincenzo et al. . |
| 5,752,823 | 5/1998 | Vogt ........................................ 433/19 |
| 5,829,975 | 11/1998 | Gold . |
| 5,897,313 | 4/1999 | Cleary et al. ........................... 433/19 |

FOREIGN PATENT DOCUMENTS

| | | |
|---|---|---|
| 2 087 079 | 12/1971 | France . |
| 2 702 141 | 9/1994 | France . |
| 44 05 086 | 7/1994 | Germany . |

OTHER PUBLICATIONS

Jasper Jumper Color Atlas, by Franz–Peter Schwindling, pp. 31–39, 78–81, 85–89, 1997.

Jasper Jumper manual, American Orthodontics, date unknown.

Eureka Spring! Clinical Information.

*Primary Examiner*—Nicholas D. Lucchesi
*Attorney, Agent, or Firm*—James D. Christoff

[57] ABSTRACT

An orthodontic force module for correcting Class II malocclusions includes a resilient body and a coupling connected to the body for connecting the body to a selected orthodontic appliance located on the patient's upper jaw. The coupling includes an opening that extends in a reference plane substantially parallel to and preferably containing the longitudinal axis of the body. The orientation of the opening provides enhanced freedom of movement of the force module when the patient's jaws are opened or closed and significantly reduces the likelihood of fracture of the coupling.

36 Claims, 3 Drawing Sheets

ORTHODONTIC FORCE MODULE WITH FRACTURE-RESISTANT COUPLING

BACKGROUND OF THE INVENTION

1. Field of the Invention

This invention relates to an intra-oral force module used in orthodontic treatment. More specifically, the present invention relates to an orthodontic force module for correcting Class II malocclusions.

2. Description of the Related Art

Orthodontic treatment involves movement of malpositioned teeth to orthodontically correct positions. During treatment, tiny orthodontic appliances known as brackets are connected to anterior, cuspid and bicuspid teeth, and an archwire is placed in a slot of each bracket. The archwire forms a track to guide movement of the brackets and the associated teeth to desired positions for correct occlusion. Typically, the ends of the archwire are held by appliances known as buccal tubes that are secured to molar teeth.

Various types of elastomeric devices, also known as force modules, are commonly used in orthodontic treatment. The resilient force of such modules in tension or compression is typically used to move a tooth or an orthodontic appliance relative to other teeth or orthodontic appliances. As one example, tiny O-ring devices are used as ligatures to secure the archwire in slots of the brackets. As another example, elongated devices, including chain-like modules having a number of interconnected O-ring portions, are sometimes stretched between selected brackets in order to move certain teeth relative to other teeth. Other devices are especially adapted to separate adjacent teeth or to rotate a tooth about its long axis.

Examples of known elastomeric devices are found in U.S. Pat. Nos. 3,530,583, 3,758,947, 4,038,753, 4,950,158 and 5,044,946. U.S. Pat. No. 5,317,074 describes improved elastomeric orthodontic force modules that are made of a material resistant to staining when exposed to foods or beverages such as mustard, tea and coffee.

The orthodontic treatment of some patients includes correction of the alignment of the upper dental arch with the lower dental arch. For example, certain patients have a condition referred to as a Class II malocclusion wherein the lower dental arch is located an excessive distance rearward of the upper dental arch when the jaws are closed. Other patients may have an opposite condition referred to as a Class III malocclusion wherein the lower dental arch is located forward of the upper dental arch when the jaws are closed.

Orthodontic treatment of Class II and Class III malocclusions are commonly corrected by movement of the upper dental arch as single unit relative to movement of the lower dental arch as a single unit. To this end, pressure is often applied to each dental arch as a unit by applying pressure to the brackets, archwires or attachments connected to the brackets or archwires. In this manner, the Class II or Class III malocclusion can be corrected at the same time that the archwires and brackets are used to move individual teeth to desired positions.

Orthodontic force modules made of an elastomeric material have been used in the past to treat a Class II malocclusion by connecting a pair of such force modules to both arches on opposite sides of the oral cavity. In such instances, the force module may be used in tension to pull the jaws together in a direction along reference lines that extend between the points of attachment of each force module. Examples of such force modules include an O-ring or a chain-type module made of a number of integrally connected O-rings.

Conventional elastomeric force modules used in treatment of a Class II or Class III malocclusion are often removable by the patient for replacement when necessary and for cleaning of the teeth. Unfortunately, neglect of the patient to reinstall the force modules seriously retards the progress of treatment. Poor cooperation from the patient can defeat timely achievement of the goals of an otherwise well-planned treatment program, resulting in an additional expenditure of time for both the patient and the orthodontist. Patient cooperation is often a problem with adolescent patients.

A number of devices that are fixed in place in the oral cavity during orthodontic treatment have been proposed in the past to overcome the problems of patient cooperation associated with removable force modules. For example, U.S. Pat. Nos. 3,798,773, 4,462,800 and 4,551,095 disclose a telescoping tube assembly that urges the jaws toward positions of improved alignment. The assemblies are fixed to other orthodontic appliances by the orthodontist, and thus problems of patient non-compliance are avoided. The device shown in U.S. Pat. No. 3,798,773 includes an internal coil compression spring to exert force on the dental arches as the mouth is closed.

A coiled wire spring device used in tension for applying corrective forces between the dental arches is shown in U.S. Pat. No. 3,618,214 and includes, in one embodiment, a pair of fasteners such as eyelets secured to opposite ends of the coiled wire spring. A protective sheath is disposed around the spring. The spring produces a restoring force upon elongation that urges the jaws toward an improved alignment.

Other orthodontic devices for correcting Class II and Class III malocclusions are described in U.S. Pat. Nos. 4,708,646 and 5,352,116. Such patents describe flexible members with swivel end attachments for connection to the upper and lower jaws of a patient. The length of the members is selected such that the member is curved in an arc when the patient's jaws are closed. The inherent bias of the members toward a normally straight orientation provides a force that pushes one jaw forwardly or rearwardly relative to the other jaw.

The commercial embodiments of the devices described in U.S. Pat. Nos. 4,708,646 and 5,352,116 include internal coil spring that are surrounded by a plastic sheath. It has been observed in some instances that the coil spring may break during use after a period of time. Unfortunately, the plastic sheath often hides the broken portion of the spring, such that it is difficult to confirm that the device is working as intended.

Other types of force modules are described in U.S. Pat. Nos. 5,435,721, 5,651,672 and 5,897,313. However, there is a continuing need to improve the state of the art so that a force module can be constructed that provides reliable corrective force as desired by the orthodontist over the expected lifetime of its use. More specifically, there is a desire to reduce as much as possible the likelihood that the force module will fracture after extended periods of use in the oral cavity, so that the treatment program is not interrupted and replacement of the module during the course of treatment is unnecessary.

SUMMARY OF THE INVENTION

The present invention is directed in one embodiment toward an orthodontic force module for correcting Class II malocclusions. The force module comprises a resilient body having a longitudinal axis. The body has a first end section, a second end section and a middle section located between the first end section and the second end section. A first coupling is connected to the first end section for connecting the first end section to a selected orthodontic appliance located on the patient's upper jaw. A second coupling is connected to the second end section for connecting the second end section to a selected orthodontic appliance located on the patient's lower jaw. The body has a length such that the middle section is bent in a curve when the patient's jaws are closed. At least one of the couplings includes an opening that extends in a reference plane substantially parallel to the longitudinal axis of the body.

Another embodiment of the invention is also directed toward an orthodontic force module for correcting Class II malocclusions. In this embodiment, the force module includes a resilient body having longitudinal axis, and the body has a first end section, a second end section and a middle section located between the first end section and the second end section. A first coupling is connected to the first end section for connecting the first end section to a selected orthodontic appliance located on the patient's upper jaw. A second coupling is connected to the second end section for connecting the second end section to a selected orthodontic appliance located on the patient's lower jaw. The first coupling includes an opening. The force module also includes a pin having a generally "L"-shaped configuration with a first leg extending in a generally lingual direction through the opening and a second leg extending in a generally mesial direction for connection to the selected orthodontic appliance located on the patient's upper jaw.

The force module in its various embodiments provides a reliable corrective force to treat Class II malocclusions, and yet also has been found to be less likely to fracture over extended periods of time in cycle testing. Advantageously, the force module in certain embodiments of the invention may be used on either the right or the left side of the oral cavity, so that two different force modules need not be manufactured, kept in inventory and sold as with many of the other force modules known in the art.

Further details of these and other aspects of the invention are set out in the detailed description that follows as well as in the accompanying drawings.

DETAILED DESCRIPTION OF THE PREFERRED EMBODIMENTS

Figure 1:
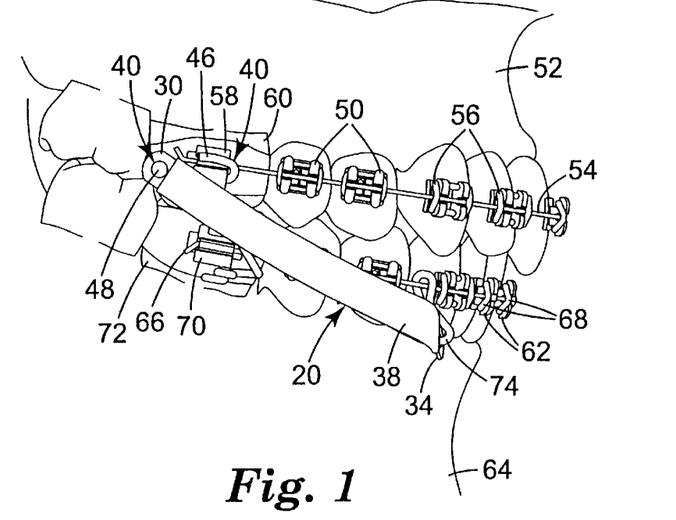
FIG. 1 is a side elevational view showing an orthodontic force module constructed in accordance with one embodiment of the present invention and installed in the oral cavity of a patient to illustrate one example of use.
Figure 2:
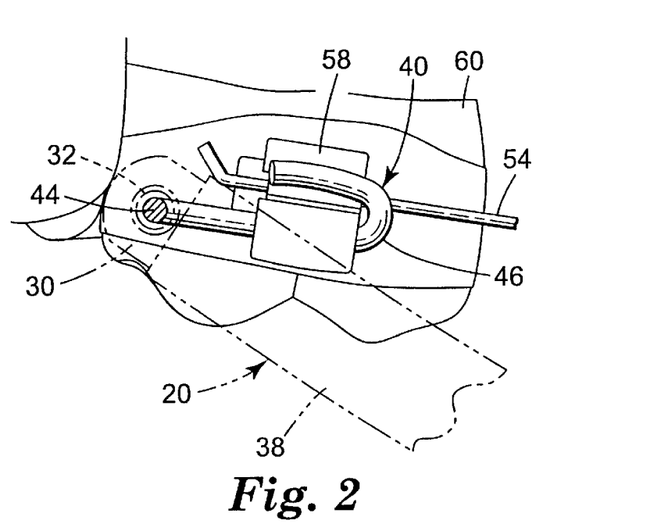
FIG. 2 is an enlarged, fragmentary view of a portion of FIG. 1, with parts of the force module broken away in section and with other parts shown in phantom lines.
Figure 3:
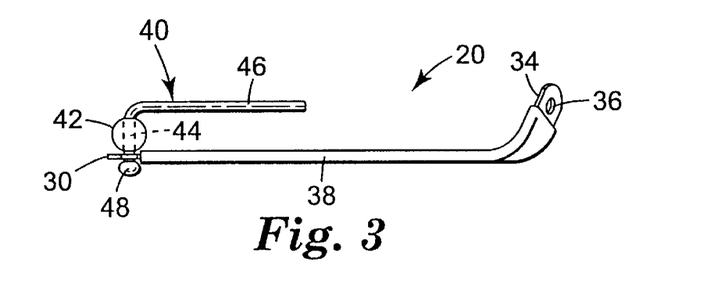
FIG. 3 is a top plan view of the orthodontic force module of FIG. 1 alone as it appears before installation in the oral cavity.
Figure 4:
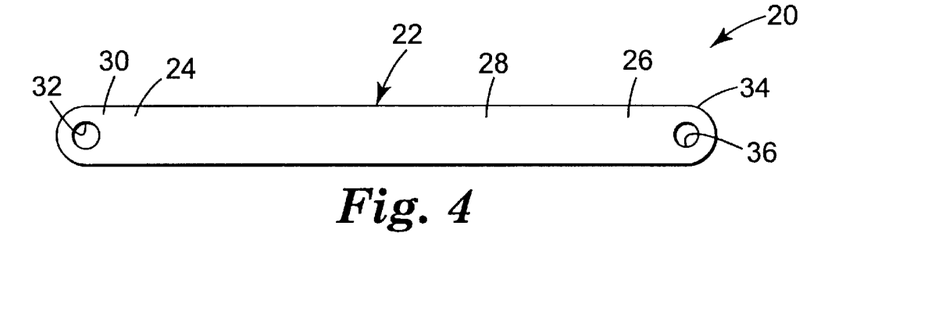
FIG. 4 is a side elevational view of part of the force module shown in FIG. 3 before a second coupling of the force module is bent during the course of manufacture.

An orthodontic force module for correcting Class II malocclusions that is constructed in accordance with one embodiment of the invention is illustrated in FIGS. 1–4 and is broadly designated by numeral 20. The force module 20 is shown for exemplary purposes in FIGS. 1 and 2 as it appears in use when installed on the right side of the patient's oral cavity. FIG. 3 shows the force module alone before installation, and FIG. 4 shows a part of the force module as it appears during an intermediate step of manufacture.

Turning now to FIG. 4, the force module 20 includes a resilient body 22 having a longitudinal axis. In this embodiment, the body 22 has a relatively constant cross-sectional configuration when viewed in reference planes perpendicular to the longitudinal axis at different locations along the longitudinal axis. The body includes a first end section 24, a second end section 26 and a middle section 28 that is located between the first end section 24 and the second end section 26.

A first coupling 30 is connected to the first end section 24 for connecting the first end section 24 to a selected orthodontic appliance located on the patient's upper jaw. The first coupling 30 includes a circular opening 32.

A second coupling 34 is connected to the second end section 26 for connecting the second end section 26 to a selected orthodontic appliance located on the patient's lower jaw. The second coupling 34 includes a circular opening 36. The openings 32, 36 may have a diameter, for example, of about 0.05 to 0.06 inch (1.3 to 1.5 mm).

Preferably, and as shown in FIG. 4, the first coupling 30 and the second coupling 34 are integrally connected to the first end section 24 and the second end section 26 respectively. As such, the body 22 and the couplings 30, 34 may be stamped from a section of resilient material such as a metallic material. Particularly preferred materials include shape-memory alloys such a near stoichiometric nickel-titanium alloy.

As shown in FIGS. 1 and 3, the second coupling 34 in this embodiment extends along a reference plane that is oriented at an obtuse angle relative to the longitudinal axis of the body 22. A presently preferred angle is about 115 degrees. If the body 22 and the second coupling 34 are integrally connected to each other and made of a metallic material, the angle of the second coupling 34 is formed during the manufacturing process by bending the second coupling 34 relative to the body 22 past the yield point of the material along a forming axis that is located at an acute angle relative to the longitudinal axis of the body 22. FIG. 4 illustrates the body 22 before bending, and FIG. 3 shows the force module 20 as it appears after the body 22 is bent.

The opening 32 of the first coupling 30 extends in a reference plane that is substantially parallel to the longitudinal axis of the body 22. Preferably, and as shown in the drawings, the first coupling 30 extends along a reference axis that is collinear with the longitudinal axis of the body 22, and the opening 32 extends in a reference plane that includes the longitudinal axis of the body 22.

Preferably, the body 22 and a portion of the couplings 30, 34 are covered by a plastic sheath 38 that is illustrated in FIGS. 1–3. Preferably, the sheath 38 is made of a resilient plastic material that is resistant to staining by food and beverages. Optionally, the sheath 38 may be made of a plastic material that shrinks upon heating so that during manufacture the body 22 may be readily inserted in the sheath 38, and the sheath 38 can then be fixed to the body 22 by use of a heat gun, heat lamp, oven or the like. As another alternative, the sheath 38 may be made by dip-coating the body 22 in a curable, liquid polymer.

The force module 20 also includes a pin 40 that is depicted in FIGS. 1–3 and stop 42 that is depicted only in FIG. 3. The pin 40 preferably has a configuration as illustrated in FIG. 3 before installation of the force module 20 in the patient's oral cavity. As shown, the pin 40 includes a first elongated leg 44 and a second elongated leg 46 that extends at an angle of approximately 90 degrees relative to the direction of extension of the first leg 44. The pin initially has an overall, generally "L"-shaped configuration.

The first leg 44 of the pin 40 extends through the first opening 32. The pin also includes an enlarged head 48 that is secured to the outer end of the first leg 44. Preferably, the head 48 is integrally connected to the first leg 44 and has a generally spherical shape, although other constructions are also possible.

The stop 42 has an internal passageway, and the first leg 44 of the pin 40 extends through the passageway. Preferably, the stop 42 has an overall, generally spherical shape. However, other shapes are also possible, including ovoids or football shapes and cylindrical sleeves.

Preferably, an outer end portion of the second leg 46 has a yield stress that is less than the yield stress of remaining portions of the pin 40. Such construction enables the outer end portion to be permanently deformed by the practitioner with less effort than would otherwise be required, and may be provided by annealing or partially annealing the outer end portion of the second leg 46. Further details for annealing or partially annealing the outer portion of the second leg 46 and alternative constructions are described in pending U.S. patent application Ser. No. 09/197,309 filed Nov. 20, 1998 and entitled "ORTHODONTIC COUPLING PIN", the disclosure of which is expressly incorporated by reference herein.

FIG. 1 illustrates the force module 20 as an example of how it might appear once installed in the oral cavity of a patient undergoing orthodontic treatment. In FIG. 1, a number of slotted orthodontic brackets 50 are fixed to teeth of a patient's upper jaw 52, and an archwire 54 is received in the slot of each bracket 50. A ligature 56 extends around each bracket 50 in order to urge the archwire 54 toward an orientation seated in the slot of each bracket 50.

In the example shown in the drawings, an orthodontic buccal tube 58 is fixed to a metallic orthodontic band that is placed around a first molar tooth 60. The buccal tube 58 includes a passage that receives an end of the archwire 54. The buccal tube 58 is shown in more detail in FIG. 2.

The buccal tube 58 also includes an auxiliary passage that receives the second leg 46 of the pin 40. Once the second leg 46 has been inserted into the auxiliary passage, the outer end portion of the second leg 46 is bent in an arc as shown in FIGS. 1 and 2 in order to releasably secure the first coupling 30 of the force module 20 to the buccal tube 58.

The stop 42 enables the pin 40 to be cinched to the buccal tube 58 in a relatively tight manner without creating binding or otherwise unduly hindering movement of the body 22 relative to the pin 40. Preferably, the stop 42 is rotatable relative to the pin 40. Alternatively, the stop 42 is fixed to the pin 40 once the first leg 44 has been inserted through the first opening 32.

A number of slotted orthodontic brackets 62 are fixed to teeth of the patient's lower jaw 64 as shown in FIG. 1. A lower archwire 66 is placed in the slot of each bracket, and a ligature 68 extends around each bracket 62 in order to urge the archwire 66 toward a seated orientation in the slot of each bracket 62. The end of the archwire 66 is received in a passage of a buccal tube 70 that is mounted on a band that encircles a patient's lower first molar tooth 72.

The second coupling 34 is connected to a selected orthodontic appliance located on the patient's lower jaw 64, such as one of the brackets 62 or the archwire 66. Preferably, the second coupling 34 is coupled to a motion-enhancing appliance such as an attachment device 74 that includes a wire segment that crosses over a labial side of the lower archwire 66 as the patient's jaws 52, 64 are opened. The attachment device 74 increases the range of free sliding motion of the force module 20 and reduces the amount of stress that might be otherwise imposed on the force module 20, on the brackets 50, 62 and/or on the archwires 54, 66 as the patient's jaws 52, 64 are opened.

The attachment device 74 as presently preferred is described in more detail in pending U.S. patent application Ser. No. 09/275,490 filed Mar. 24, 1999 and entitled "ORTHODONTIC ATTACHMENT DEVICE FOR INTER-ARCH APPLIANCES", the disclosure of which is expressly incorporated by reference herein. In brief, the attachment device 74 includes a mesial closed loop that extends about the lower archwire 66, and a distal end section that extends through a passage of the buccal tube 70. The attachment device 74 includes an intermediate segment that passes through the second opening 36. Further aspects of the attachment device 74, as well as alternative constructions, are described in the aforementioned pending U.S. patent application Ser. No. 09/275,490.

The body 22 has a length selected such that the middle section 28 is bent in a curve when the patient's jaws 52, 64 are closed and the force module 20 is used to correct a Class II malocclusion. Suitable lengths include, for example, about 28 mm to about 38 mm as measured from the center-to-center distance of the openings 32, 36.

The construction of the force module 20 has been found to present significant advantages over known force modules. In cycle testing, it has been found that alignment of the first coupling 30 in straight, collinear orientation with the longitudinal axis of the body 22 reduces the likelihood of fracture in areas adjacent the opening 32 after extended periods of time. While some of the devices known in the art have proven to operate in satisfactory manner in the majority of treatments, it is a significant benefit to further increase the reliability of the force modules so that the likelihood of fracture can be reduced as much as possible. Additionally, the coplanar, straight alignment of the first coupling 30 with the body 22 simplifies manufacture when the body 22 and the couplings 30, 34 are made of a unitary section of metallic material, in that the first coupling 30 need not be bent in an arc as known in the past.

The parallel, collinear alignment of the first coupling 30 with the longitudinal axis of the body 22 also provides greater freedom of movement of the force module 20 when the patient's jaws are opened and closed. By aligning the reference plane of the opening 32 in a direction perpendicular to a reference axis that extends through the patient's upper molar tooth 60 in a buccal-lingual direction (i.e., in a direction extending from the patient's cheek to the patient's tongue), the body 22 can freely swivel with a simple hinging motion as the patient's jaws 52, 64 are opened and closed with little, if any, restriction of movement. Moreover, the second leg 46 of the pin 40 can pivot along its longitudinal axis in the passage of the buccal tube 58, to further enhance free swinging movement of the force module 20 as the patient's jaws 52, 64 are opened or closed.

Figure 5:
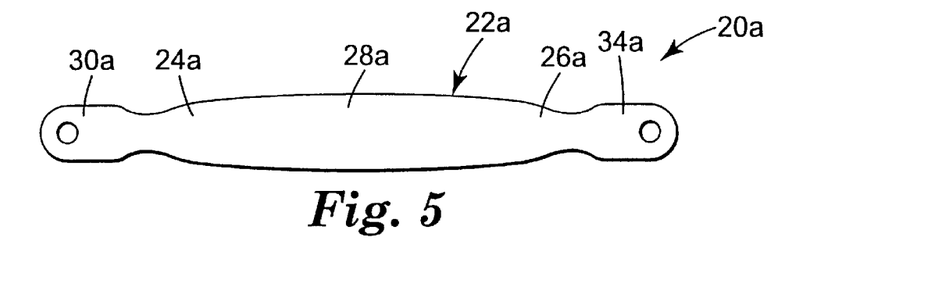
FIG. 5 is a view somewhat similar to FIG. 4, but depicting a force module constructed in accordance with another embodiment of the invention.

A force module 20a for correcting Class II malocclusions according to another embodiment of the invention is illustrated in FIG. 5. The force module 20a is essentially the same as the force module 20, except for the differences as noted below.

The force module 20a includes a body 22a. The body 22a includes a first end section 24a, a second end section 26a and a middle section 28a located between the first end section 24a and the second end section 26a. A first coupling 30a is connected to the first end section 24a, and a second coupling 34a is connected to the second end section 26a.

The middle section 28a has a cross-sectional area in reference planes perpendicular to the longitudinal axis of the body 22a that decreases as the first end section 24a and the second end section 26a are approached. If, for example, the body 22a and the couplings 30a, 34a are stamped from a unitary, flat section of metallic material, the sections 24a, 26a, 28a will have cross-sectional shapes of generally rectangular configurations with uniform thickness. However, the width of the rectangular cross-sectional shape of the middle section 28a will be wider than the rectangular cross-sectional shape of the end sections 24a, 26a, and will decrease in width as the end sections 24a, 26a are approached.

In FIG. 5, the force module 20a is shown as it appears before the second coupling 34a is bent in an arc relative to the longitudinal axis of the body 22a, similar to the view shown in FIG. 4. Additionally, and although not shown in the drawings, the force module 20a is preferably provided with a pin and stop somewhat similar or identical to the pin 40 and stop 42 described above. The force module 20a may also include a plastic sheath somewhat similar to the sheath 38 described above.

Figure 6:
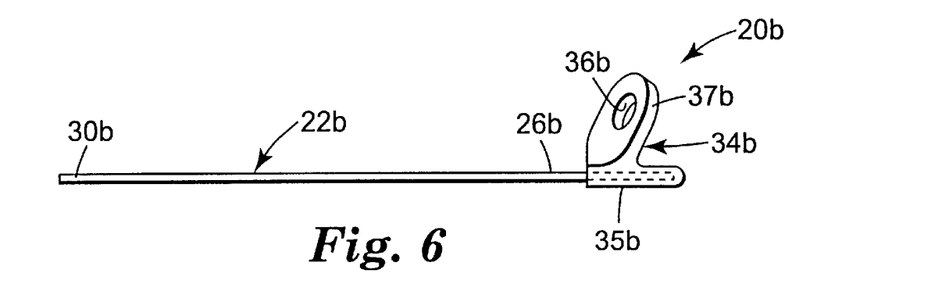
FIG. 6 is a view somewhat similar to FIG. 3, but showing a force module constructed in accordance with yet another embodiment of the invention, and wherein a pin of the force module is not illustrated.
Figure 7:
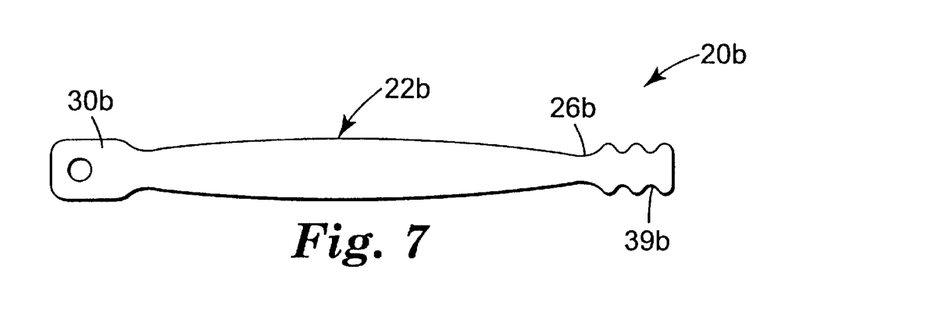
FIG. 7 is a side elevational view of the force module shown in FIG. 6 except that a second coupling of the force module has been omitted.

A force module 20b constructed in accordance with another embodiment of the invention is illustrated in FIGS. 6 and 7. The force module 20b includes a body 22b that is identical to the body 22a. Additionally, the force module 20b includes a first coupling 30b that is identical to the first coupling 30a.

The force module 20b includes a second coupling 34b that, in this embodiment, is somewhat different than the second couplings 34, 34a. The second coupling 34b is initially separate from the body 22b and includes a sleeve portion 35b and an arm portion 37b. The sleeve portion 35b receives a coupling extension of a second end section 26b of the body 22b. The coupling extension of the second end section 26b is shown in FIG. 7 and includes a series of notches 39b.

The second coupling 34b may be made from a variety of materials (including plastics or metals) and may be made using any suitable technique. For example, the coupling 34b may be made of stainless steel that is cast or metal-injection molded, and the swaged, staked or pinned in place in non-removable fashion to the body 22b. Alternatively, the coupling 22b may be made of a plastic material that is molded in place around the coupling extension of the second end section 26b or molded separately from the body 22b and then bonded in place with an adhesive. The notches 39b facilitate a fixed, secure connection between the body 22b and the coupling 34b.

The arm portion 37b extends along a reference axis that is oriented at an obtuse angle relative to the longitudinal axis of the body 22b as well as to the direction of extension of the sleeve portion 35b. Preferably, that obtuse angle is about 115 degrees. The arm portion 37b also includes a circular opening 36b that is used in a manner similar to use of the openings 36, 36a.

Figure 8:
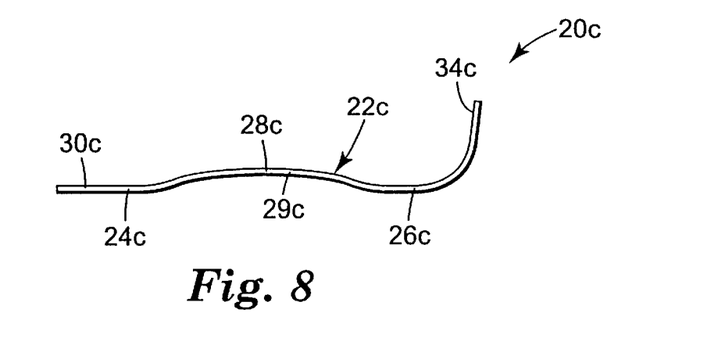
FIG. 8 is a top plan view of part of a force module constructed in accordance with still another embodiment of the invention.

An orthodontic force module 20c according to another embodiment of the invention is illustrated in part in FIG. 8. The force module 20c is essentially the same as the force module 20 with the exception of the differences described below. The force module 20c includes a body 22c having a first end section 24c, a second end section 26c and a middle section 28c located between the first end section 24c and the second end section 26c. The middle section 28c may have a cross-sectional area in reference planes perpendicular to the longitudinal axis of the body 22c that is either constant or decreases as the end sections 24c, 26c are approached.

The force module 20c has a first coupling 30c and a second coupling 34c that are essentially identical to the couplings 30, 34 respectively described above. The second coupling 34c is bent about a forming axis that extends at an acute angle relative to the longitudinal axis of the body 22c. However, the view in FIG. 8 is taken along the forming axis (instead of along an axis perpendicular to the longitudinal axis as shown in FIG. 3) and as such the flat face of the second coupling 34c is not visible in FIG. 8.

The middle section 28c includes a recurve portion 29c that is preferably centered along the middle of the length of the body 22c. As shown, the recurve portion 29c extends along an arc that is oppositely oriented relative to the curved arc that extends between the body 22c and the second coupling 34c. The recurve portion 29c is visible whenever the body 22c is in its normal, relaxed orientation.

Although not shown in FIG. 8, the force module 20c also preferably includes a pin and stop similar to the pin 40 and stop 42. Additionally, a sheath may be provided over the body 22c, somewhat similar to the sheath 38 described above.

Figure 9:
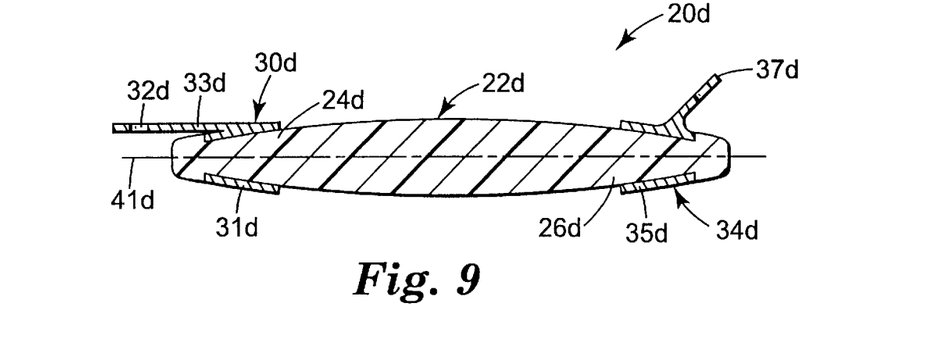
FIG. 9 is a side cross-sectional view of an orthodontic force module constructed in accordance with still another embodiment of the invention.

An orthodontic force module 20d according to another embodiment of the invention is illustrated in FIG. 9. The force module 20d includes an elongated body 22d that is made of an elastomeric material. Preferably, the elastic material exhibits resistance to staining by food and beverages, and is similar to the elastomeric material described in the aforementioned U.S. Pat. No. 5,897,313.

The force module 20d includes a first coupling 30d and a second coupling 34d. Each of the couplings 30d, 34d has a sleeve portion 31d, 35d respectively that is somewhat similar in shape to a hollow, truncated cone. The body 22d includes a first end section 24d that extends through the sleeve portion 31d, and a second end section 26d that extends through the sleeve portion 35d.

Each of the end sections 24d, 26d terminates in an outer, enlarged head having an outer diameter that is larger than the passageway of the adjacent sleeve portion 31d, 35d. The heads present a shoulder that retains the couplings 30d, 34d in secure connection with the adjacent end sections 24d, 26d.

The first coupling 30d includes an arm portion 33d that is integrally connected to the sleeve portion 31d, and the arm portion 33d presents an opening 32d. The opening 32d is circular. The arm portion 33d and the opening 32d both lie in a reference plane that is parallel to a longitudinal axis 41d of the body 22d when the latter is in its normal, relaxed, straight orientation.

The second coupling 34d includes an arm portion 37d that is integrally connected to the sleeve portion 35d. The arm portion 37d extends at an obtuse angle relative to the longitudinal axis 41d of the body 22d. Preferably, that obtuse angle is about 135 degrees, although other angles are also possible. Preferably, both of the couplings 30d, 34d are pivotally movable relative to the body 22d in an arc about the axis 41d.

Optionally, the force module 20d may be used on either the right side of the oral cavity or the left side of the oral cavity without alteration. However, the practitioner may elect to first slightly pivot the coupling 30d relative to the coupling 34d in an arc about the axis 41d to optimize fitting and use.

Figure 10:
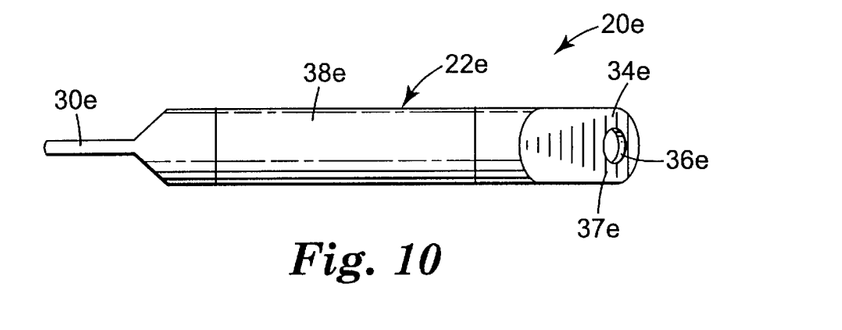
FIG. 10 is a top plan view of an orthodontic force module constructed in accordance with an additional embodiment of the invention.
Figure 11:
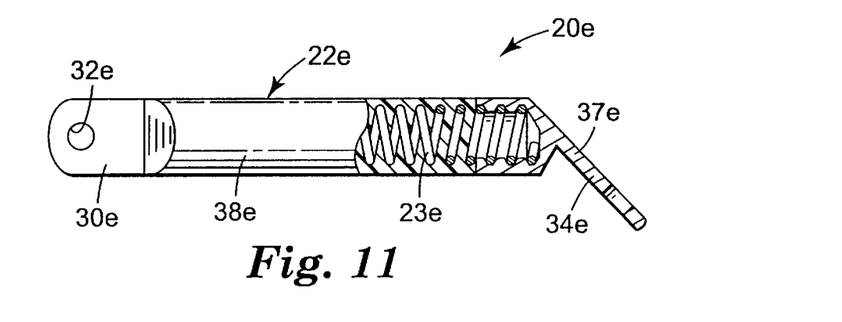
FIG. 11 is a side elevational view in partial section of the orthodontic force module depicted in FIG. 10.

An orthodontic force module 20e constructed in accordance with another embodiment of the invention is illustrated in FIGS. 10 and 11. The force module 20e includes an elongated, normally straight body 22e that includes an inner coil spring 23e (FIG. 11) that is preferably made of a metallic material such as stainless steel or a shape-memory alloy such as a near stochiometric nickel-titanium alloy. The spring 23e is preferably covered by a sheath 38e. Optionally, the sheath 38e is injection-molded around the spring 23e by an insert molding process.

The force module 20e also includes a first coupling 30e and a second coupling 34e. The first coupling 30e extends in a reference plane that contains the longitudinal axis of the body 22e when the latter is in its normal, relaxed configuration. The first coupling 30e includes a circular opening 32e that lies in a reference plane that is parallel or that contains the longitudinal axis of the body 22e when the latter is in its normal, relaxed orientation.

The force module 20e also includes a second coupling 34e with an arm portion 37e. As shown, the arm portion 37e extends at an obtuse angle relative to the longitudinal axis of the body 22e when the latter is in its relaxed orientation. The arm portion 37e includes a circular opening 36e.

Preferably, the force module 20e includes a pin and stop similar or identical to the pin 40 and stop 42 described above. Preferably, one or both of the couplings 30e, 34e is pivotally movable relative to the body 22e in an arc about the longitudinal axis of the body 22e.

As with the force module 20d, the force module 20e may be used on either the right side or the left side of the patient's oral cavity without alteration. However, the practitioner may opt to first slightly pivot the coupling 34e relative to the coupling 30e in an arc about the longitudinal axis of the force module 20e to optimize fitting and use.

Those individuals skilled in the art may recognize that a variety of modifications and additions to the presently preferred embodiments are possible without departing from the spirit of the invention. For example, the force modules 20–20e may be constructed so that both of the couplings extend in reference planes parallel to or containing the longitudinal axis of the body. In that instance, it may be desirable to provide the body with a slight curvature when relaxed or to provide other structure that ensures that the body will preferentially bend in a certain direction when the patient's jaws are closed.

Other variations are also possible. For example, the force modules 20, 20a, 20b, 20c, 20d may have other aspects such as described in U.S. Pat. Nos. 5,897,313 and 5,651,672. Similarly, the force module 20e may have other aspects or features, such as the aspects or features described in U.S. Pat. Nos. 4,708,646 and 5,352,116, both of which are incorporated by reference herein. Accordingly, the invention should not be deemed limited by the embodiments described in detail above, but only by a fair reading of the claims that follow along with their equivalents.

What is claimed is:

1. An orthodontic force module for correcting Class II malocclusions comprising:
   a resilient body having a longitudinal axis, the body having an upper first end section, a lower second end section and a middle section located between the first end section and the second end section;
   a first coupling connected to the first end section for connecting the first end section to a selected orthodontic appliance located on the patient's upper jaw; and
   a second coupling connected to the second end section for connecting the second end section to a selected orthodontic appliance located on the patient's lower jaw, wherein the body has a length such that the middle section is bent in a curve along the longitudinal axis when the patient's jaws are closed to provide a force for correcting a Class II malocclusion, and wherein the first coupling is located in distal relation to the second coupling and includes an opening that extends in a reference plane substantially parallel to the longitudinal axis of the body.

2. An orthodontic force module according to claim 1 wherein the opening extends in a reference plane that contains the longitudinal axis of the body.

3. The orthodontic force module of claim 1 wherein the first coupling has an opening that extends in a reference plane substantially parallel to the longitudinal axis of the body and is located distally of the second coupling when the force module is connected to the patient's jaws.

4. An orthodontic force module of claim 1 wherein the first coupling is integrally connected to the first end section.

5. An orthodontic force module according to claim 1 wherein the middle section has an inherent bias toward a normally straight orientation.

6. An orthodontic force module according to claim 1 wherein the body has a generally flat shape with a generally rectangular cross-sectional configuration in reference planes perpendicular to the longitudinal axis of the body.

7. An orthodontic force module according to claim 6 wherein the middle section has a cross-sectional area in reference planes perpendicular to the longitudinal axis of the body that decreases as the first end section and the second end section are approached.

8. An orthodontic force module according to claim 6 wherein the middle section has a cross-sectional area in reference planes perpendicular to the longitudinal axis of the body that is generally constant as the first end section and the second end section are approached.

9. An orthodontic force module according to claim 1 wherein the body has a generally circular shape in reference planes perpendicular to the longitudinal axis of the body.

10. An orthodontic force module according to claim 9 wherein the middle section has a cross-sectional area in reference planes perpendicular to the longitudinal axis of the body that decreases as the first end section and the second end section are approached.

11. An orthodontic force module according to claim 1 wherein at least one end section has a generally flat configuration and extends in a reference plane substantially parallel to the longitudinal axis of the body.

12. An orthodontic force module according to claim 11 wherein at least one end section extends in a reference plane that contains the longitudinal axis of the body.

13. An orthodontic force module according to claim 1 and including a pin having a generally overall "L"-shaped configuration, wherein the pin extends through the opening.

14. An orthodontic force module according to claim 13 and including a stop, and wherein the pin extends through the stop.

15. An orthodontic force module according to claim 14 wherein the stop has a generally spherical shape.

16. An orthodontic force module according to claim 14 wherein the stop has a generally cylindrical configuration.

17. An orthodontic force module according to claim 13 wherein the pin includes a first leg that extends in a generally lingual direction and a second leg that extends in a generally mesial direction when the orthodontic force module is connected to the patient's jaws.

18. An orthodontic force module according to claim 1 wherein the body is comprised of an elastomeric material.

19. An orthodontic force module according to claim 1 wherein the body is comprised of a metallic material.

20. An orthodontic force module according to claim 19 wherein the metallic material is a shape-memory alloy.

21. An orthodontic force module according to claim 1 wherein the second coupling includes a sleeve portion that receives the second end section.

22. An orthodontic force module according to claim 21 wherein the sleeve portion is crimped to the second end section.

23. An orthodontic force module according to claim 1 wherein the first coupling is movable relative to the body in an arc about the longitudinal axis of the body.

24. An orthodontic force module according to claim 1 wherein at least one of the couplings includes a through passageway and wherein the body extends through each through passageway, the body including an enlarged head located outwardly of each passageway.

25. An orthodontic force module according to claim 1 wherein the middle section includes a recurve portion.

26. An orthodontic force module for correcting Class II malocclusions comprising:
a resilient body having a longitudinal axis, the body having an upper first end section, a lower second end section and a middle section located between the first end section and the second end section;
a first coupling connected to the first end section for connecting the first end section to a selected orthodontic appliance located on the patient's upper jaw, wherein the first coupling includes an opening;
a second coupling connected to the second end section for connecting the second end section to a selected orthodontic appliance located on the patient's lower jaw, wherein the first coupling is located in distal relation to the second coupling; and
a pin having a generally overall "L"-shaped configuration, the pin having a first leg extending through the opening in a generally lingual direction and a second leg extending through the orthodontic appliance on the patient's upper jaw in a generally mesial direction when the force module is connected to the patient's jaws, wherein the second leg extends at an angle of approximately 90 degrees relative to the direction of extension of the first leg, and wherein the body has a length such that the middle section is bent in a curve along the longitudinal axis when the patient's jaws are closed to provide a force for correcting a Class II malocclusion.

27. An orthodontic force module according to claim 26 wherein the opening extends in a reference plane that contains the longitudinal axis of the body.

28. An orthodontic force module according to claim 26 wherein the first coupling is integrally connected to the first end section.

29. An orthodontic force module according to claim 26 wherein the body has a generally flat shape with a generally rectangular cross-sectional configuration in reference planes perpendicular to the longitudinal axis of the body.

30. An orthodontic force module according to claim 29 wherein the middle section has a cross-sectional area in reference planes perpendicular to the longitudinal axis of the body that decreases as the first end section and the second end section are approached.

31. An orthodontic force module according to claim 26 wherein the body has a generally circular shape in reference planes perpendicular to the longitudinal axis of the body.

32. An orthodontic force module according to claim 31 wherein the middle section has a cross-sectional area in reference planes perpendicular to the longitudinal axis of the body that decreases as the first end section and the second end section are approached.

33. An orthodontic force module according to claim 26 wherein the at least one end section has a generally flat configuration and extends in a reference plane substantially parallel to the longitudinal axis of the body.

34. An orthodontic force module according to claim 26 wherein the body in comprised of an elastomeric material.

35. An orthodontic force module according to claim 26 wherein the body is comprised of a shape-memory alloy.

36. An orthodontic force module according to claim 26 wherein the second coupling includes a sleeve portion that receives the second end section.

\* \* \* \* \*

UNITED STATES PATENT AND TRADEMARK OFFICE
CERTIFICATE OF CORRECTION

PATENT NO.: 6,053,730
DATED: April 25, 2000
INVENTOR(S): James D. Cleary It is certified that error appears in the above-identified patent and that said Letters Patent is hereby corrected as shown below:

In col. 8, line 5 "the" should read ---then---.

Signed and Sealed this

First Day of May, 2001

Attest:

NICHOLAS P. GODICI

Attesting Officer    Acting Director of the United States Patent and Trademark Office